United States Patent
Martin

(10) Patent No.: US 7,122,578 B2
(45) Date of Patent: Oct. 17, 2006

(54) METHOD AND COMPOSITION FOR TREATING MAMMALIAN DISEASES AND INJURIES WHICH CAUSE PAIN, ERYTHEMA, SWELLING, CRUSTING, ISCHEMIA SCARRING AND EXCESS WHITE BLOOD CELL INFILTRATION

(76) Inventor: Alain Martin, 31 Country Club Dr., Ringoes, NJ (US) 08551

( * ) Notice: Subject to any disclaimer, the term of this patent is extended or adjusted under 35 U.S.C. 154(b) by 243 days.

(21) Appl. No.: 09/950,490

(22) Filed: Sep. 11, 2001

(65) Prior Publication Data

US 2003/0165457 A1    Sep. 4, 2003

(51) Int. Cl.
*A61K 31/20* (2006.01)
*A61K 31/19* (2006.01)
*A61K 31/56* (2006.01)
*A61K 9/00* (2006.01)

(52) U.S. Cl. .............. 514/560; 514/557; 514/558; 514/559; 514/170; 424/400

(58) Field of Classification Search ........ 514/558, 514/559, 560, 557, 170; 424/400
See application file for complete search history.

(56) References Cited

U.S. PATENT DOCUMENTS

| 5,648,380 A | * | 7/1997 | Martin | 514/461 |
| 5,767,156 A | * | 6/1998 | Ferrante et al. | 514/560 |
| 5,863,938 A | * | 1/1999 | Martin | |
| 6,429,229 B1 | * | 8/2002 | Bouyssou et al. | 514/561 |
| 6,943,190 B1 | * | 9/2005 | Fink et al. | 514/456 |

* cited by examiner

*Primary Examiner*—Shengjun Wang
(74) *Attorney, Agent, or Firm*—Craig M. Bell

(57) ABSTRACT

A method for treating the disease state in mammals caused by mammalian cells involved in the inflammatory response is disclosed. Mammalian cells participating in the inflammatory response are contacted with an inflammatory suppressor selected from the group consisting of alpha-keto acids and their salts which reduce the undesired inflammatory response and is an antioxidant. The inflammatory suppressor may further provide a cellular energy source and be a building block in the cellular synthesis of other cellular components. Compositions for reducing and treating undesired inflammatory response such as pain, swelling, erythema, crusting, scarring, itching, also disclosed.

14 Claims, No Drawings

METHOD AND COMPOSITION FOR TREATING MAMMALIAN DISEASES AND INJURIES WHICH CAUSE PAIN, ERYTHEMA, SWELLING, CRUSTING, ISCHEMIA SCARRING AND EXCESS WHITE BLOOD CELL INFILTRATION

FIELD OF THE INVENTION

This invention pertains to therapeutic methods of preventing, and the treatment and repair of damaged cells and tissues from injuries and the resulting disease states in mammals caused by the inflammatory production of pain, erythema, itching, crusting, swelling, an inflammatory response to radiation, excess angiogenesis (capillary formation), tissue ischemia and scarring which produce uncontrolled scarring and reduced healing. This invention also pertains to compositions used in the therapeutic methods to enhance the proper collagen and elastin deposition in wounds and injuries.

BACKGROUND OF THE INVENTION

Wounds are internal or external bodily injuries or lesions caused by mechanical, chemical, viral, bacterial or thermal means, which disrupt the normal continuity of structures. Such bodily injuries include contusions, which are wounds in which the skin is unbroken, incisions, i.e., wounds in which the skin is broken by a cutting instrument, and lacerations, which are wounds in which the skin is broken by a dull or blunt instrument. Patients who suffer major wounds could benefit from an antiscarring wound healer enhancer, that protects and enhances repair while reducing the pain, swelling, tissue ischemia, excess angiogenesis, erythema (redness), crusting, itching, and fibrotic conditions (scarring) which accompany most wounds.

Wound healing consists of a series of processes whereby injured tissues are repaired, specialized tissue is generated, and new tissue is reorganized. Wound healing consists of three major phases: (a) an inflammation phase (0–3 days), (b) a cellular proliferation phase (3–12 days), and (c) a remodeling phase (3–6 months).

During the inflammation phase, platelet aggregation and clotting form a matrix which traps plasma proteins and blood cells to induce the influx of various types of cells. During the cellular proliferation phase, new connective or granulation tissue and blood vessels are formed. During the remodeling phase, granulation tissue is replaced by a network of collagen and elastin fibers leading to the formation of scar tissue. Most wounds also produce pain, swelling, itching, ischemia, crusting, erythema, and scarring, all of which are undesirable.

When cells are injured or killed as a result of a wound, a wound-healing step is desirable to resuscitate the injured cells and produce new cells to replace the dead cells. The healing process requires the reversal of cytotoxicity, the suppression of inflammation, the stimulation of cellular viability and proliferation and reduced scarring. Wounds require low levels of oxygen in the initial stages of healing to suppress oxidative damage and higher levels of oxygen in the later stages of healing to promote collagen formation by fibroblasts.

Wounds produce oxygen radicals. Mammalian cells are continuously exposed to activated oxygen species such as superoxide ($O_2-$), hydrogen peroxide ($H_2O_2$), hydroxyl radicals (OH), and singlet oxygen ($^1O_2$). In vivo, these reactive oxygen intermediates are generated by cells in response to aerobic metabolism, catabolism of drugs and other xenobiotics, ultraviolet and x-ray radiation, and the respiratory burst of phagocytic cells (such as white blood cells) to kill invading bacteria introduced through wounds. Hydrogen peroxide, for example, is produced during respiration of most living organisms especially by stressed and injured cells.

These active oxygen species can injure cells. An important example of such damage is lipid peroxidation which involves the oxidative degradation of unsaturated lipids. Lipid peroxidation is highly detrimental to membrane structure and function and can cause numerous cytopathological effects. Cells defend against lipid peroxidation by producing radical scavengers such as superoxide dismutase, catalase, and peroxidase. Injured cells have a decreased ability to produce radical scavengers. Excess hydrogen peroxide can react with DNA to cause backbone breakage of the DNA, produce mutations, as well as the alteration and liberation of the bases. Hydrogen peroxide can also react with pyrimidines to open the 5,6-double bond, which inhibits the ability of pyrimidines to hydrogen bond to complementary bases, Hallaender, et al. (1971). Such oxidative biochemical injury can result in the loss of cellular membrane integrity, reduced enzyme activity, changes in transport kinetics, changes in membrane lipid content, and leakage of potassium ions, amino acids, other cellular material, and the formation of excess keloid and scar formation.

Inflammation is a nonspecific response caused by a variety of injuries including the penetration of the host by an infectious agent. The distinguishing feature of inflammation is the dilation and increased permeability of minute blood vessels. The inflammatory response consists of three successive phases: (a) increased vascular permeability with resulting edema, pain, and swelling, (b) cellular infiltration and phagocytoses, and (c) proliferation of the fibroblasts synthesizing new connective tissue to repair the injury. A large number of mediators of inflammation have been implicated in the inflammatory process primarily in terms of their capacity to induce vasodilatation and increased permeability. Inflammation also increases levels of compounds that increase pain, erythema, ischemia, excess angiogenesis, swelling, crusting, itching, and scarring.

Direct injury, such as that caused by toxins produced by microorganisms, leads to destruction of vascular endothelium and results in the increased permeability to plasma proteins, especially in the venules and venular capillaries. Mediators of secondary injury are liberated from the site of direct injury. As a result, gaps form between vascular endothelial cells through which plasma proteins escape. Granulocytes, monocytes, and erythrocytes may also leave vascular channels. Mediators of secondary injury include unknown substances and histamine, peptides (kinins), kinin-forming enzymes (kininogenases), and a globulin permeability factor. These mediators are blocked from action by antihistamines and sympathoamines, and are most pronounced in effect on venules, although lymph-vascular endothelium also becomes more porous as a part of secondary injury. In the early stages of inflammation, the exudate is alkaline and neutrophilic polymorphonuclear leukocytes predominate. As lactic acid accumulates, presumably from glycolysis, the pH drops and macrophages become the predominant cell type. Lactic acid and antibodies in the inflammatory exudate may inhibit parasites, but the major anti-infectious effect of the inflammatory response is attributable to phagocytic cells.

The beneficial effect of the inflammatory response is the production of:

(1) leukocytes in great numbers; (2) plasma proteins, non-specific and specific humoral agents, fibrinogen that on conversion to fibrin aids in the localization of the infectious process while acting as a matrix for phagocytoses; and (3) increased blood and lymph flow that dilutes and flushes toxic materials while causing a local increase in temperature.

The initial increase in capillary permeability and vasodilatation in an inflamed wound is followed by an increase in metabolism of the tissues. Leakage of fibrinogen into the wound, where proteolytic enzymes convert it into fibrin thrombi, establishes a capillary and lymphatic blockade. The concentrations of components of the ground substance of connective tissue collagen, mucopolysaccharides, glycoproteins, and nonfibrous proteins are greatly increased during this process. As the exudative phase of the inflammation subsides, the fibroblast is found to be the dominant cell in the wounded zone. The fibroblast first proliferates, then synthesizes extracellular material, including new collagen fibers and acid mucopolysaccharides, which are laid down to form the new tissue matrix.

On a macroscopic level, the inflammatory phenomenon is usually accompanied by the familiar clinical signs of erythema, swelling, edema tenderness (hyperalgesia), and pain. During this complex response, chemical mediators such as histamine, 5-hydroxytryptamine (5-HT), slow-reacting substance of anaphylaxis (SRS-A), various chemotactic factors, bradykinin, and prostaglandins are liberated locally. Phagocytic cells migrate into the area, and cellular lysosomal membranes may be ruptured, releasing lytic enzymes. All these events may contribute to the inflammatory response.

The production of reactive oxygen intermediates has been suggested to cause many skin, tissue, and organ disorders such as atherosclerosis, arthritis, cytotoxicity, skin inflammation, photoaging, wrinkling, actinic keratosis, tumor formation, cancer, hypertension, Parkinson's Disease, lung disease, and heart disease. The role of active oxygen radicals in promoting tumors has been based on the findings that (a) tumor promoters increase the level of oxygen radicals, (b) many free radical-generating systems promote tumors, and (c) certain antioxidants inhibit the biochemical effects of tumor promoters.

In vitro, reactive oxygen intermediates can be generated in cellular culture media by auto-oxidation and photo-oxidation of media components. During excision and storage, transplant organs can suffer oxidative injuries which result in the loss of cellular membrane integrity and shorten the usable life of the organ.

When cells are stressed by oxidative injury, a resuscitation step is necessary to re-condition the cells. Antioxidants have been shown to inhibit damage associated with active oxygen species. For example, pyruvate and other alpha-keto acids have been reported to react rapidly and stoichiometrically with hydrogen peroxide to protect cells from adverse cytolytic effects, O'Donnell-Tormey, et al., *J. Exp. Med.*, 165, pp. 500–514 (1987).

U.S. Pat. No. 5,210,098, issued to Nath disclose a method to arrest or prevent acute kidney failure by administration of a non-toxic pyruvate salt to a patient in need of such treatment.

The Nath '098 invention provides a therapeutic method comprising the administration of an amount of a pyruvate salt to a patient experiencing or in danger of, acute renal failure. The pyruvate salt, preferably sodium pyruvate, is dispersed or dissolved in a pharmaceutically acceptable liquid carrier and administered parenterally in an amount effective to arrest or prevent said acute renal failure, thus permitting restoration of normal kidney function. In some cases, the pyruvate may be infused directly into the kidney or into the proximal renal arterial circulation. The method is effective to prevent or counter-act acute kidney failure due to a wide variety of causes, including, but not limited to, traumatic injury including burn injury and obstruction; reperfusion following ischemia, inflammatory glomerulonephritis, and sepsis, e.g., due to gram negative bacterial infection.

U.S. Pat. No. 5,296,370, issued to Martin, et al. 1994, discloses therapeutic compositions for preventing and reducing injury to mammalian cells and increasing the resuscitation rate of injured mammalian cells. In one embodiment, the therapeutic composition comprises (a) a pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells.

U.S. Pat. No. 5,256,697, issued to Miller, et al., discloses a method for orally administering a therapeutically effective amount of a pyruvate precursor to a mammal to improve insulin resistance, lower lasting insulin levels and reduce fat gain.

U.S. Pat. Nos. 3,920,835; 3,984,556, and 3,988,470, all issued to Van Scott, et al. disclose methods for treating acne, dandruff, and palmar keratosis, respectively, which consist of applying to the affected area a topical composition comprising from about 1% to about 20% of a lower aliphatic compound containing from two to six carbon atoms selected from the group consisting of alpha-hydroxy acids, alpha-keto acids and esters thereof, and 3-hydroxybutryic acid in a pharmaceutically acceptable carrier. The aliphatic compounds include pyruvic acid and lactic acid.

U.S. Pat. Nos. 4,105,783 and 4,197,316, both issued to Yu, et al., disclose a method and composition, respectively, for treating dry skin which consists of applying to the affected area a topical composition comprising from about 1% to about 20% of a compound selected from the group consisting of amides and ammonium salts of alpha-hydroxy acids, beta-hydroxy acids, and alpha-keto acids in a pharmaceutically acceptable carrier. The compounds include the amides and ammonium salts of pyruvic acid and lactic acid.

U.S. Pat. No. 4,234,599, issued to Van Scott, et al., discloses a method for treating actinic and non-actinic skin keratoses which consists of applying to the affected area a topical composition comprising an effective amount of a compound selected from the group consisting of alpha-hydroxy acids, beta-hydroxy acids, and alpha-keto acids in a pharmaceutically acceptable carrier. The acidic compounds include pyruvic acid and lactic acid.

U.S. Pat. No. 4,294,852, issued to Wildnauer, et al., discloses a composition for treating skin which comprises the alpha-hydroxy acids, beta-hydroxy acids, and alpha-keto acids disclosed above in combination with $C_3$–$C_8$ aliphatic alcohols.

U.S. Pat. No. 4,663,166, issued to Veech, discloses an electrolyte solution which comprises a mixture of L-lactate and pyruvate in a ratio from 20:1 to 1:1, respectively, or a mixture of D-beta-hydroxybutyrate and acetoacetate, in a ratio from 6:1 to 0.5:1, respectively.

Sodium pyruvate has been reported to reduce the number of erosions, ulcers, and hemorrhages on the gastric mucosa in guinea pigs and rats caused by acetylsalicylic acid. The analgesic and antipyretic properties of acetylsalicylic acid were not impaired by sodium pyruvate, Puschmann, *Arzneimittelforschung*, 33, pp. 410–415 and 415–416 (1983).

Pyruvate has been reported to exert a positive inotropic effect in stunned myocardium which is a prolonged ventricular dysfunction following brief periods of coronary artery occlusions which does not produce irreversible damage, Mentzer, et al., *Ann. Surg.*, 209, pp. 629–633 (1989). Pyruvate has also been reported to produce a relative stabilization of left ventricular pressure and heart work parameter and to reduce the size of infarctions. Pyruvate improves resumption of spontaneous beating of the heart and restoration of normal rates and blood pressure development, Bunger, et al., *J. Mol. Cell. Cardiol.*, 18, pp. 423–438 (1986), Mochizuki, et al., *J. Physiol. (Paris)*, 76, pp. 805–812 (1980), Regitz, et al., *Cardiovasc. Res.*, 15 pp. 652–658 (1981), Giannelli, et al., *Ann. Thorac. Surg.*, 21 pp. 386–396 (1976).

Sodium pyruvate has been reported to act as an antagonist to cyanide intoxication (presumably through the formation of cyanohydrin) and to protect against the lethal effects of sodium sulfide and to retard the onset and development of functional, morphological, and biochemical measures of acrylamide neuropathy of axons, Schwartz, et al., *Toxicol. Appl. Pharmacol.*, 50 pp. 437–442 (1979), Sabri, et al., *Brain Res.*, 483, pp. 1–11 (1989).

U.S. Pat. No. 5,798,388, issued to Katz discloses a method and compositions for the treatment of pulmonary diseases resulting from inflammation consisting of the administration of pyruvate, lactate, and precursor thereof and their salts in a pharmaceutically acceptable carrier. The compositions may also be a cellular energy source.

A chemotherapeutic cure of advanced L1210 leukemia has been reported using sodium pyruvate to restore abnormally deformed red blood cells to normal. The deformed red blood cells prevented adequate drug delivery to tumor cells, Cohen, *Cancer Chemother. Pharmacol.*, 5, pp. 175–179 (1981).

Primary cultures of heterotopic tracheal transplant exposed in vivo to 7,12-dimethylbenz(a)anthracene were reported to be successfully maintained in enrichment medium supplemented with sodium pyruvate along with the cultures of interleukin-2 stimulated peripheral blood lymphocytes, and plasmacytomas and hybridomas, pig embryos, and human blastocysts, Shacter, *J. Immunol, Methods*, 99, pp. 259–270 (1987), Marchok, et al., *Cancer Res.*, 37, pp. 1811–1821 (1977), Davis, *J. Reprod. Fertil, Suppl.*, 33, pp. 115–124 (1985), Okamoto, et al., *No To Shinkei*, 38, pp. 593–598 (1986), Cohen, et al., *J. In vitro Fert. Embryo Transfer*, 2, pp. 59–64 (1985).

U.S. Pat. Nos. 4,158,057; 4,351,835; 4,415,576, and 4,645,764, all issued to Stanko, disclose methods for preventing the accumulation of fat in the liver of a mammal due to the ingestion of alcohol, for controlling weight in a mammal, for inhibiting body fat while increasing protein concentration in a mammal, and for controlling the deposition of body fat in a living being, respectively. The methods comprise administering to the mammal a therapeutic mixture of pyruvate and dihydroxyacetone, and optionally riboflavin. U.S. Pat. No. 4,548,937, issued to Stanko, discloses a method for controlling the weight gain of a mammal which comprises administering to the mammal a therapeutically effective amount of pyruvate, and optionally riboflavin. U.S. Pat. No. 4,812,479, issued to Stanko, discloses a method for controlling the weight gain of a mammal which comprises administering to the mammal a therapeutically effective amount of dihydroxyacetone, and optionally riboflavin and pyruvate.

Rats fed a calcium-oxalate lithogenic diet including sodium pyruvate were reported to develop fewer urinary calculi (stones) than control rats not given sodium pyruvate, Ogawa, et al., *Hinvokika Kivo*, 32, pp. 1341–1347 (1986).

U.S. Pat. No. 4,521,375, issued to Houlsby, discloses a method for sterilizing surfaces which come into contact with living tissue. The method comprises sterilizing the surface with aqueous hydrogen peroxide and then neutralizing the surface with pyruvic acid.

U.S. Pat. No. 4,416,982, issued to Tauda, et al., discloses a method for decomposing hydrogen peroxide by reacting the hydrogen peroxide with a phenol or aniline derivative in the presence of peroxidase. U.S. Pat. No. 4,696,917, issued to Lindstrom, et al., discloses an irrigation solution which comprises Eagle's Minimum Essential Medium with Earle's salts, chondroitin sulfate, a buffer solution, 2-mercaptoethanol, and a pyruvate. The irrigation solution may optionally contain ascorbic acid and alpha-tocopherol. U.S. Pat. No. 4,725,586, also issued to Lindstrom, et al., discloses an irrigation solution which comprises a balanced salt solution, chondroitin sulfate, a buffer solution, 2-mercaptoethanol, sodium bicarbonate or dextrose, a pyruvate, a sodium phosphate buffer system, and cystine. The irrigation solution may optionally contain ascorbic acid and gammatocopherol.

U.S. Pat. No. 4,847,069, issued to Bissett, et al., discloses a photoprotective composition comprising (a) a sorbohydroxamic acid, (b) an anti-inflammatory agent selected from steroidal anti-inflammatory agents and a natural anti-inflammatory agent, and (c) a topical carrier. Fatty acids may be present as an emollient. U.S. Pat. No. 4,847,071, also issued to Bissett, et al., discloses a photoprotective composition comprising (a) a tocopherol or tocopherol-ester radical scavenger, (b) an anti-inflammatory agent, and (c) a topical carrier. U.S. Pat. No. 4,847,072, issued to Bissett, et al., discloses a topical composition comprising not more than 25% tocopherol sorbate in a topical carrier.

U.S. Pat. No. 5,863,938, issued to Martin, discloses a therapeutic antibacterial wound-healing composition comprising an effective amount of an antibacterial agent and a wound-healing composition consisting of (a) pyruvate- or keto-glutaric acid (b) an antioxidant, and (c) a mixture of fatty acids.

U.S. Pat. No. 5,561,157, issued to Yu, et al., discloses a composition and method for the therapeutic treatment of age spots, wrinkles, dry skin, eczema, psoriasis, and keratosis, using alpha- and beta-keto-carboxylic acids and their salts.

U.S. Pat. No. 6,149, 924, issued to Paul discloses the use of many agents that increase the production of skin lipids, increase barrier function, hydrogen peroxide neutralization, prevention of loss of moisturizing factor from the skin. The agents are amino acids and their breakdown products.

U.S. Pat. No. 5,536,751, issued to Bunger discloses a pharmaceutical composition as an active phosphorylation potential enhancing substance using an alpha-keto-carboxylic acid, primarily pyruvate.

The addition of sodium pyruvate to bacterial and yeast systems has been reported to inhibit hydrogen peroxide production, enhance growth, and protect the systems against the toxicity of reactive oxygen intermediates. The optimum ratio of unsaturated to saturated fatty acids contained within chicken fat enhanced membrane repair and reduced cytotoxicity. The anti-oxidants gluthathione and thio-glycollate reduced the injury induced by oxygen radical species.

While the above therapeutic compositions and methods are reported to inhibit the production of reactive oxygen intermediates and enhance healing, none of the compositions and methods treat the damage and resulting disease state in mammals caused by undesired pain, progressive tissue ischemia, excess angiogenesis, excess white blood cell (WBC) infiltration, erythema, swelling, itching, crusting, and scarring. Moreover, cellular signaling agents in mammalian cells are needed to deposit the correct ratio and type of collagen and elastin. The new teachings involve the use of alpha-keto acids with unique properties, singly or in combination to treat different types of injuries.

SUMMARY OF THE INVENTION

This invention pertains to therapeutic wound-healing compositions useful for reducing the size, duration and severity of non-infected and infected wounds, and reducing scarring, inflammation, pain, crusting, tissue ischemia, excess angiogenesis, excess WBC infiltration, swelling and erythema. More particularly, the wound-healing compositions comprise an agent or agents that enhances healing, while reducing wound pain, erythema, swelling, itching, ischemia, excess WBC infiltration, excess angiogenesis, and crusting and a therapeutic wound-healing composition and/or its metabolites. This invention also pertains to methods for preparing and using the enhanced wound-healing compositions and the pharmaceutical products in which the therapeutic compositions may be used to stimulate fibroblasts to deposit the correct type and ratio of collagen and elastin, reduce scarring and is an antioxidant A preferred embodiment of the therapeutic wound-healing composition of this invention comprises (a) a keto-isovalerate selected from the group consisting of keto-isovalerate acid, pharmaceutically acceptable salts of keto-isovalerate acid, and mixtures thereof, singly or in combination with other keto acids alone to produce the desired effect or in combination with (b) an antioxidant, and (c) a mixture of saturated and unsaturated fatty acids wherein the fatty acids are those fatty acids required for the repair of cellular membranes and resuscitation of mammalian cells.

The healing agent in addition to reducing the undesired inflammatory response and being an antioxidant may further provide a cellular energy source and be a building block in the cellular synthesis of other cellular components. The healing agent may also increase cellular metabolic rate.

The present invention also pertains to compositions for reducing and treating the disease state in mammals caused by undesired inflammatory response comprising: an inflammatory response suppressor and a carrier composition wherein the inflammatory response suppressor is an antioxidant and capable of reducing undesired inflammatory conditions in mammalian cells.

The inflammatory response suppressor or suppressors may be used individually or in combination with a therapeutic agent such as an antibacterial, antiviral, antifungal, protein, enzyme, antihistamine, hormone, nonsteriodal antiinflammatory, cytokine, steroid, antioxidant, fatty acids and membrane stabilizing agents.

A preferred method of administering the inflammatory suppressor is by injection or topical application.

DETAILED DESCRIPTION OF THE INVENTION

This invention pertains to the use of a therapeutic wound-healing agent alone or in combination with other agents (keto acids) that reduces wound inflammation, pain, swelling, erythema, scarring, tissue ischemia, excess angiogenesis, excess WBC infiltration, itching, and crusting. In one embodiment, the wound-healing composition comprises (a) keto-isovalerate selected from the group consisting of keto-isovalerate acid, and/or its pharmaceutically acceptable salts, singly or and mixtures thereof, in combination with other keto acids from which they can be combined to produce the desired effect. These compounds can be further combined with (b) an antioxidant; and (c) a mixture of saturated and unsaturated fatty acids wherein the fatty acids are those fatty acids required for the repair of cellular membranes and resuscitation of mammalian cells. In another embodiment, various other keto acids can be combined to produce the desired effect to enhance healing. Each keto acid has its own unique healing characteristics and in combination they work synergistically to enhance healing by reducing wound inflammation, pain, swelling, erythema, scarring, tissue ischemia, excess angiogenesis, excess WBC infiltration, itching, and crusting.

The present invention then, comprises novel therapeutic wound-healing compositions for preventing and reducing injury to mammalian cells and increasing the resuscitation rate of injured mammalian cells, while reducing the undesired pain, swelling, progressive tissue ischemia, excess angiogenesis, excess WBC infiltration, erythema, itching, scarring, and crusting. Not all tissue wounds are the same and different wounds require different therapeutic approaches. Some produce more or less scarring, pain, swelling, itching, erythema, ischemia, WBC infiltration, and inflammation. Cells treated with the therapeutic wound-healing compositions of the present invention show decreased levels of hydrogen peroxide production, increased resistance to cytotoxic agents, increased rates of proliferation, increased viability and an increase in the deposition of the correct type and ratio of collagen and elastin without scar formation. Cellular cultures containing the therapeutic wound-healing compositions showed enhanced differentiation and proliferation over control cultures and these rapidly formed attachments or tight junctions between the cells to form an epidermal sheet. Wounded mammals treated with the therapeutic wound-healing compositions show significantly improved wound closing and healing over untreated mammals and mammals treated with conventional healing compositions. The wound-healing compositions may be used alone or in combination with other medications.

The therapeutic wound-healing compositions comprise several different embodiments. In one embodiment, the therapeutic wound-healing composition comprises (a) a keto-isovalerate selected from the group consisting of keto-isovalerate acid, and its pharmaceutically acceptable salts, singly and or in combination with other keto acids to achieve the desired effect depending on the wound or injury type or disease state. These can be made into mixtures with, (b) an antioxidant, and (c) a mixture of saturated and unsaturated fatty acids wherein the fatty acids are those fatty acids required for the repair of cellular membranes and resuscitation of mammalian cells.

The therapeutic wound-healing compositions of this invention may be further combined with a therapeutically effective amount of an antibacterial agent to form an antibacterial-wound-healing composition. The antibacterialwound-healing composition may be used alone or in combination with other medicaments. This invention also pertains to methods for preparing and using the antibacterial-wound-healing composition and the pharmaceutical products in which the therapeutic composition may be used.

The therapeutic antibacterial-wound-healing composition of this invention may be further combined with one or more additional medicaments for treating wounds to form augmented antibacterial-wound-healing compositions. This invention also relates to methods for preparing and using the augmented therapeutic antibacterial-wound-healing compositions and the pharmaceutical products in which the augmented compositions may be used.

The term "injured cell" as used herein means a cell that has any cellular activity disrupted for any reason. For example, an injured cell may be a cell that has injured membranes or damaged DNA, RNA, and/or ribosomes. For example, a cell which has (a) injured membranes so that transport through the membranes is diminished resulting in an increase in toxins and normal cellular wastes inside the cell and a decrease in nutrients and other components necessary for cellular repair inside the cell (b) an increase in concentration of oxygen radicals inside the cell because of the decreased ability of the cell to produce antioxidants and enzymes, or (c) damaged DNA, RNA, and ribosomes which must be repaired or replaced before normal cellular functions can be resumed. The term "resuscitation" of injured mammalian cells as used herein means the reversal of cytotoxicity, the stabilization of the cellular membrane, an increase in the proliferation rate of the cell, and/or the normalization of cellular functions such as the secretion of growth factors, hormones, and the like. The term "cytotoxicity" as used herein means a condition caused by a cytotoxic agent that injures the cell. Injured cells do not readily proliferate because injured cells expend all energy on cellular repair. Aiding cellular repair promotes cellular proliferation.

The term "pro-drug," as used herein, refers to compounds which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound which upon in vivo enzymatic attack will liberate the parent compound. The chemical alterations of the parent compound are such that the change in physiochemical properties will affect the drug's absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms pro-drugs, latentiated drugs, and bioreversible derivatives are used interchangeably. By inference, latentiation implies a time lag element or time component involved in regenerating the bioactive parent molecule in vivo. The term pro-drug is general in that it includes latentiated drug derivatives as well as those substances which are converted after administration to the actual substance which combines with receptors. The term pro-drug is also a generic term for agents which undergo biotransformation prior to exhibiting their pharmacological actions. In the case where the administered drug is not the active agent, but rather is biotransformed to the active agent, the term "pro-drug" also includes compounds which may not necessarily undergo biotransformation to the administered drug but may undergo biotransformation to the active agent which exhibits the desired pharmacological effect.

The term "metabolite, as used herein, refers to any substance produced by metabolism or by a metabolic process. "Metabolism," as used herein, refers to the various chemical reactions involved in the transformation of molecules or chemical compounds occurring in tissue and the cells therein.

The cells which may be treated with the therapeutic wound-healing compositions of the present invention are mammalian cells. Although the present therapeutic wound-healing compositions are useful for treating mammalian epidermal keratinocytes and mammalian monocytes, applicant contemplates that the therapeutic wound-healing compositions may also be used to protect or resuscitate all mammalian cells. Keratinocytes are representative of normal mammalian cells and are the fastest proliferating cells in the body. The correlation between the reaction of keratinocytes to injury and therapy and that of mammalian cells in general is very high. Monocytes are representative of specialized mammalian cells such as the WBC in the immune system and the organ cells in liver, kidney, heart, and brain. The mammalian cells may be treated in vivo and in vitro.

Epidermal keratinocytes are the specialized epithelial cells of the epidermis which synthesize keratin, a scleroprotein which is the principal constituent of epidermis, hair, nails, horny tissue, and the organic matrix of the enamel of teeth. Mammalian epidermal keratinocytes constitute about 95% of the epidermal cells and together with melanocytes form the binary system of the epidermis. In its various successive stages, epidermal keratinocytes are also known as basal cells, prickle cells, and granular cells.

Monocytes are mononuclear phagocytic leukocytes which undergo respiratory bursting and are involved in reactive oxygen-mediated damage within the epidermis. Leukocytes are WBC or corpuscles which may be classified into two main groups: granular leukocytes (granulocytes) which are leukocytes with abundant granules in the cytoplasm and nongranular leukocytes (nongranulocytes) which are leukocytes without specific granules in the cytoplasm and which include the lymphocytes and monocytes. Phagocytic cells are cells which ingest microorganisms or other cells and foreign particles. Monocytes are also known as large mononuclear leukocytes, and hyaline or transitional leukocytes.

Epidermal keratinocytic cells and monocytic cells have multiple oxygen generating mechanisms and the degree to which each type of mechanism functions differs in each type of cell. In monocytes, for example, the respiratory bursting process is more pronounced than in epidermal keratinocytes. Hence, the components in the therapeutic wound-healing compositions of the present invention may vary depending upon the types of cells involved in the condition being treated.

As set out above, in a first embodiment of the present invention, the therapeutic wound-healing composition for treating mammalian cells, preferably epidermal keratinocytes, comprises (a) a keto-isovalerate selected from the group consisting of keto-isovalerate acid, and the pharmaceutically acceptable salts of keto-isovalerate acid, singly or mixtures or in combination with other keto acids which can be further combined with (b) an antioxidant, and (c) a mixture of saturated and unsaturated fatty acids wherein the fatty acids are those fatty acids required for the repair of cellular membranes and the resuscitation of mammalian cells.

Alpha-keto-isovalerate $(CH_3)_2CHCOCOOH$ is a fundamental intermediate in protein synthesis, i.e., the biosynthesis of the amino acids leucine, valine and their metabolism. The formation of leucine begins by condensation of alpha-keto-isovaleric acid (which is also the precursor of valine) with acetyl CoA to yield alpha-isopropylmalic acid. The subsequent steps are similar to those leading from citric acid to keto-glutaric acid in the tricarboxylic acid cycle. The two major sources of acetyl coenzyme A are derived from the metabolism of glucose and fatty acids. Glycolysis consists of a series of transformations wherein each glucose molecule is transformed in the cellular cytoplasm into two molecules of pyruvic acid. Pyruvic acid may then enter the mitochondria where it is oxidized by coenzyme A in the presence of enzymes and cofactors to acetyl coenzyme A. Pyruvic acid can also be converted in several steps to keto-isovaleric acid leading to the formation of valine.

Oxaloacetate has been shown to inhibit keloid formation, angiogenesis, and excess infiltration of leukocytes. Its properties can be used in burns to prevent progressive burn ischemia due to thermal injuries which causes delayed tissue loss in surrounding healthy tissue. It reacts with $H_2O_2$ to produce malonate, a competitive inhibitor of succinate dehydrogenase, which effectively inhibits respiration. When used in combination with keto-isovalerate or pyruvate on burns, excess WBC infiltration is reduced and healing is enhanced. It can be used to treat patients undergoing radiation therapy to inhibit regrowth of the tumor, while at the same time healing normal cells.

Keto-isovalerate inhibits pain, erythema, itching and swelling. It is known to react with $H_2O_2$ to produce isobutyric acid and seems to reduce prostaglandins. Keto-butyrate is a superior moisturizing agent over all the other keto acids. It reacts with $H_2O_2$ to produce propionic acid which has been shown to be an anti-fungal agent and can be used with other keto acids to enhance the moisture in tissues. Keto-glutarate is taken up by neurons and fibroblasts and therein increases neuron survival and collagen deposition by fibroblasts. In combination with pyruvate, this keto acid produced the greatest neuron survival and regeneration. It reacts with $H_2O_2$ to produce succinic acid which inhibits mast cells from releasing histamines. Keto-caproate will disrupt cellular membranes and mucus. It reacts with $H_2O_2$ to produce valerate, a food source. It can be used with oxaloacetate to inhibit cancer cells from growing while at the same time allowing normal cells to grow. Keto-adipate dissolves excess mucus. It reacts with $H_2O_2$ to produce glutaric acid.

It is the purpose of this invention then to use these keto acids alone or in combination to enhance the healing of various types of wounds. Each wound is unique and burns are different than cuts. A further object to the present invention is to formulate various types of keto acid combinations to treat the different injuries. The goal of the present invention is that realizing that not all keto acids are equal and that each has its own unique properties, the combination of various keto acids can be used to act synergistically to treat different types of wounds more successfully than their use singly. Nothing in the known prior art has, characterized each keto acids strength or weaknesses nor has it been taught that they are therapeutically effective either singly or in combination.

The keto-isovalerate acids of the present invention may be selected from the group consisting of keto-isovalerate acid, its' pharmaceutically acceptable salts, pro-drugs of keto-isovalerate acid, and mixtures thereof. In general, the pharmaceutically acceptable salts of keto-isovalerate acid may be alkali salts and alkaline earth salts. Preferably, the keto-isovalerate is selected from the group consisting of keto-isovalerate acid, lithium keto-isovalerate, sodium keto-isovalerate, potassium keto-isovalerate, magnesium keto-isovalerate, calcium keto-isovalerate, zinc keto-isovalerate, manganese keto-isovalerate, methyl keto-isovalerate, and mixtures thereof. More preferably, the keto-isovalerate is selected from the group consisting of keto-isovalerate acid, lithium keto-isovalerate, sodium keto-isovalerate, and potassium most preferably, the keto-isovalerate is sodium keto-isovalerate.

The inflammatory suppressor agents are selected from a group consisting of keto-isovalerate, keto-isovalerate precursors, and alpha-keto-acids having three or more carbon atoms, precursors of alpha-keto acids having three or more carbon atoms and their salts. The salts of the other keto acids are listed above. The precursors of keto-isovalerate and the other alpha-keto acids may be selected from a group containing a keto acid attached to glycine, alanine, leucine, valine, isoleucine, phenylaline, amides, or to any other amino acid or compound. The keto acids having three or more carbon atoms may be selected from a group consisting of pyruvic acid, oxaloacetic acid, keto-glutaric acid, keto-butyric acid, keto-adipic acid, keto-caproic acid and their salts and mixtures thereof along with their attachments to any amino acid or other compound.

The amount of keto-isovalerate present in the therapeutic wound-healing compositions of the present invention is a therapeutically effective amount. A therapeutically effective amount of keto-isovalerate is that amount of keto-isovalerate necessary to prevent and reduce injury to mammalian cells and/or increase the resuscitation rate of injured mammalian cells. The exact amount of keto-isovalerate that is effective is a matter of preference that is determined by such factors as the type of condition being treated as well as the other ingredients incorporated in the composition. In a preferred embodiment, keto-isovalerate is present in the therapeutic wound-healing composition in an amount from about 0.1% to about 50%, preferably from about 0.2% to about 45%, and more preferably from about 0.5% to about 20% by weight of the therapeutic wound-healing composition.

Antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention may be selected from the group consisting of all forms of vitamin A (retinal), all forms of vitamin B (3,4-didehydroretinol), all forms of carotene such as alpha-carotene, β-carotene (beta, β-carotene), gamma-carotene, delta-carotene, all forms of vitamin C (D-ascorbic acid, L-ascorbic acid), all forms of tocopherol such as vitamin E (alpha-tocopherol, 3,4-dihydro-2,5,7,8-tetramethyl-2-(4,8,12-trimethyltri-decyl)-2H-1-benzopyran-6-ol), β-tocopherol, gamma-tocopherol, delta-tocopherol, tocoquinone, tocotrienol, and vitamin E esters which readily undergo hydrolysis to vitamin E such as vitamin E acetate and vitamin E succinate, and pharmaceutically acceptable vitamin E salts such as vitamin E phosphate, pro-drugs of vitamin A, carotene, vitamin C, and vitamin E, pharmaceutically acceptable salts of vitamin A, carotene, vitamin C, alpha-lipoic acid and vitamin E, and the like, and mixtures thereof. Preferably, the antioxidant is selected from the group of lipid-soluble antioxidants consisting of vitamin A,β-carotene, vitamin E, vitamin E acetate, and mixtures thereof. More preferably, the antioxidant is vitamin E or vitamin E acetate. Most preferably, the antioxidant is vitamin E acetate.

The amount of antioxidant present in the therapeutic wound-healing compositions of the present invention is also that which is a therapeutically effective amount. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients in the composition. In a preferred embodiment, the antioxidant is present in the therapeutic wound-healing composition in an amount from about 0.1% to about 40%, preferably from about 0.2% to about 30%, and more preferably from about 0.5% to about 20%, by weight of the therapeutic wound-healing composition.

The mixture of saturated and unsaturated fatty acids in the present invention are those fatty acids required for the repair of mammalian cellular membranes and the production of new cells. Fatty acids are carboxylic acid compounds found in animal and vegetable fat and oil. Fatty acids are classified as lipids and are composed of chains of alkyl groups containing from 4 to 22 carbon atoms, 0–3 double bonds and characterized by a terminal carboxyl group, —COOH. Fatty acids may be saturated or unsaturated and may be solid, semisolid, or liquid. The most common saturated fatty acids are butyric acid ($C_4$), lauric acid ($C_{12}$), palmitic acid ($C_{16}$), and stearic acid ($C_{18}$). Unsaturated fatty acids are usually derived from vegetables and consist of alkyl chains containing from 16 to 22 carbon atoms and 0–3 double bonds with the characteristic terminal carboxyl group. The most common unsaturated fatty acids are oleic acid, linoleic acid, and linolenic acid (all $C_{18}$ acids).

In general, the mixture of saturated and unsaturated fatty acids required for the repair of mammalian cellular membranes in the present invention may be derived from animal and vegetable fats and waxes, pro-drugs of saturated and unsaturated fatty acids useful in the present invention, and mixtures thereof. For example, the fatty acids in the therapeutic wound-healing composition may be in the form of mono-, di-, or triglycerides, or free fatty acids, or mixtures thereof, which are readily available for the repair of injured cells. Cells produce the chemical components and the energy required for cellular viability and store excess energy in the form of fat. Fat is adipose tissue stored between organs of the body to furnish a reserve supply of energy. The preferred animal fats and waxes have a fatty acid composition similar to that of human fat and the fat contained in human breast milk. The preferred animal fats and waxes may be selected from the group consisting of human fat, chicken fat, cow fat (defined herein as a bovine domestic animal regardless of sex or age), sheep fat, horse fat, pig fat, and whale fat. The more preferred animal fats and waxes may be selected from the group consisting of human fat. Mixtures of other fats and waxes, such as vegetable waxes (especially sunflower oil), marine oils (especially shark liver oil), and synthetic waxes and oils, which have a fatty acid composition similar to that of animal fats and waxes, and preferably to that of human fats and waxes, may also be employed.

In a preferred embodiment, the mixture of saturated and unsaturated fatty acids has a composition similar to that of human fat and comprises the following fatty acids: butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, and gadoleic acid. Preferably, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, and gadoleic acid are present in the mixture in about the following percentages by weight, respectively (carbon chain number and number of unsaturations are shown parenthetically, respectively): 0.2%–0.4% ($C_4$), 0.1% ($C_6$), 0.3%–0.8% ($C_8$), 2.2%–3.5% ($C_{10}$), 0.9%–5.5% ($C_{12}$), 2.8%–8.5% ($C_{14}$), 0.1%–0.6% ($C_{14:1}$), 23.2%–24.6% ($C_{16}$), 1.8%–3.0% ($C_{16:1}$), 6.9%–9.9% ($C_{18}$), 36.0%–36.5% ($C_{18:1}$), 20%–20.6% ($C_{18:2}$), 7.5%–7.8% ($C_{18:3}$), 1.1%–4.9% ($C_{20}$), and 3.3%–6.4% ($C_{20:1}$).

In another preferred embodiment, the mixture of saturated and unsaturated fatty acids is typically chicken fat comprising the following fatty acids; lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid. Preferably, lauric acid, myristic acid, myristoleic acid, pentadeconoic acid, palmitic acid, palmitoleic acid, margaric acid, margaroleic acid, stearic, oleic acid, linoleic acid, linolenic acid, arachidic acid, and gadoleic acid are present in the mixture in about the following percentages by weight, respectively: 0.1% ($C_{12}$), 0.8% ($C_{14}$), 0.2% ($C_{14:1}$), 0.1% ($C_{15}$), 25.3% ($C_{16}$), 7.2% ($C_{16:1}$), 0.1% ($C_{17}$), 0.1% ($C_{17:1}$), 6.5% ($C_{18}$), 37.7% ($C_{18:1}$), 20.6% ($C_{18:2}$), 0.8% ($C_{18:3}$), 0.2% ($C_{20}$), and ($C_{20:1}$, all percentages ±10%.

In another preferred embodiment, the mixture of saturated and unsaturated fatty acids comprises lecithin. Lecithin (phosphatidylcholine) is a phosphatide found in all living organisms (plants and animals) and is a significant constituent of nervous tissue and brain substance. Lecithin is a mixture of the diglycerides of stearic, palmitic, and oleic acids, linked to the choline ester of phosphoric acid. The product of commerce is predominantly soybean lecithin obtained as a by-product in the manufacturing of soybean oil. Soybean Lecithin contains palmitic acid 11.7%, stearic 4.0%, palmitoleic 8.6%, oleic 9.8%, linoleic 55.0%, linolenic 4.0%, $C_{20}$ to $C_{22}$ acids (includes arachidonic) 5.5%. Lecithin may be represented by the formula:

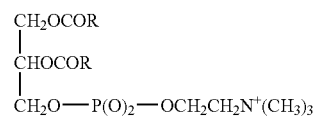

wherein R is selected from the group consisting of stearic, palmitic, and oleic acid.

The above fatty acids and percentages thereof present in the fatty acid mixture are given as an example. The exact type of fatty acid present in the fatty acid mixture and the exact amount of fatty acid employed in the fatty acid mixture may be varied in order to obtain the result desired in the final product and such variations are now within the capabilities of those skilled in the art without the need for undue experimentation.

The amount of fatty acids present in the therapeutic wound-healing compositions of the present invention is a therapeutically effective amount. A therapeutically effective amount of fatty acids is that amount of fatty acids necessary to prevent and reduce injury to mammalian cells or increase the resuscitation rate of injured mammalian cells. The exact amount of fatty acids employed is subject to such factors as the type and distribution of fatty acids employed in the mixture, the type of condition being treated, and the other ingredients in the composition. In a preferred embodiment, the fatty acids are present in the therapeutic wound-healing composition in an amount from about 1.0% to about 50%, preferably from about 2.0% to about 45%, and more preferably from about 2.5% to about 40%, by weight of the therapeutic wound-healing composition.

The combination of an antibacterial agent and the wound-healing compositions of the present invention provides a pharmaceutical composition useful for treating infected as well as non-infected wounds with an enhanced ability to prevent and reduce injury to mammalian cells and further increase the resuscitation rate of injured mammalian cells while reducing scarring. The tissue damage associated with many bacterial diseases is believed to be caused by the production of cellular produced, active oxygen species. The combination of the antibacterial agent and the wound-healing compositions may suppress such reactive oxygen-linked tissue injury.

The antibacterial agents which may be employed in the antibacterial-wound-healing therapeutic compositions may be selected from a wide variety of water-soluble and water-insoluble drugs and their acid addition or metallic salts. Both organic and inorganic salts may be used provided the antibacterial agent maintains its medicament value. The antibacterial agents may be selected from a wide range of therapeutic agents and mixtures of therapeutic agents which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillins, polypeptides, tetracyclines, cephalosporins, chloramphenicol, and clidamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furozolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, ampicillin and amoxicillin; the polypeptides, such as bacitracin and polymycin; the tetracyclines, such as tetracycline, chlorotetracycline, oxytetracycline, and doxycycline; the cephalosporins, such as cephalexin and cephalothin; and miscellaneous antibiotics, such as chloramphenicol, and clidamycin. More preferably, the antibacterial agent is selected from the group consisting of bismuth aluminate, bismuth subcitrate, bismuth subgalate, bismuth subsalicylate, sulfonamides, nitrofurazone, nitrofurantoin, furozolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymycin, polymyxin, tetracycline, chlorotetracycline, oxytetracycline, doxycycline, cephalexin, cephalothin, chloramphenicol, and clidamycin.

The antibacterial agents of the present invention may be used in many distinct physical forms well known in the pharmaceutical art to provide an initial dosage of the antibacterial agent and/or a further time-release form of the antibacterial agent. Without being limited thereto, such physical forms include free forms, encapsulated forms, and mixtures thereof.

The amount of antibacterial agent which may be employed in the antibacterial-wound-healing therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the antibacterial-wound-healing composition is present in an amount from about 0.01% to about 10%, preferably from about 0.1% to about 5%, and more preferably from about 1% to about 3% by weight of the wound-healing composition.

Therapeutic compositions and a method for treating wounds and the disease state in mammals caused by mammalian cells involved in inflammation have been discovered. The mammalian cells primarily responsible for the inflammatory response are WBC or leucocytes.

In a method for treating wounds, injuries, and disease state in mammals caused by mammalian cells involved in the inflammatory response, mammalian cells are contacted with an inflammatory suppressor. The inflammatory suppressor agent is present in an amount capable of reducing the undesired inflammatory response. The agent is an antioxidant, which reduces inflammation, pain, erythema, swelling, progressive tissue ischemia, excess WBC infiltration, excess angiogenesis, crusting, itching and scarring while stimulating fibroblasts to deposit the correct ratio and type of collagen and elastin.

The inflammatory response, often referred to as respiratory bursting, is the response of defensive mammalian cells, primarily WBC or leucocytes. These cells normally respond to an injury or invasion of the mammal by releasing a number of active compounds at the injury or invasion site. Among the compounds released are enzymes such as proteases and active oxygen species such as hydrogen peroxide.

A purpose of the respiratory burst is to provide a battery of oxidizing agents in response to a stimulant that can be used by the leucocytes for the destruction of foreign cells, viruses, particulates and some toxins which have been ingested by or are in the vicinity of the leucocyte. The term "respiratory burst" refers to a coordinated series of metabolic events that take place when leucocytes are exposed to appropriate stimuli. This group of events underlies all oxygen dependent killings by leucocytes.

The first of these events is the sharp increase in oxygen uptake that occurs upon stimulation of the leucocytes. While oxygen consumption by resting leucocytes varies widely by cell type, all respond to appropriate stimuli with an increase in oxygen uptake.

Stimulation of the leucocyte also causes an increase in glucose oxidation via the hexose monophosphate shunt. The hexose monophosphate shunt is a metabolic pathway in which glucose is oxidized to carbon dioxide and a five-carbon sugar, with NADP+ serving as electron acceptor. Activation of the hexose monophosphate shunt therefore means that the oxidation of NADPH to NADP+ increases during the respiratory burst.

The respiratory burst produces superoxide and hydrogen peroxide. Oxygen taken up by the respiratory burst is converted to superoxide. Hydrogen peroxide appears to arise during the respiratory burst mainly from the dismutation of superoxide anion.

$$2O^2 + 2H^+ \rightarrow H_2O_2 + O_2$$

It has been demonstrated by Root and Metcalf and reported in *J. Clin. Invest.* 60:1266 that 80 percent of the superoxide is converted to hydrogen peroxide, and this dismutation reaction is the only important source of the hydrogen peroxide generated during the burst. Hydrogen peroxide and superoxide are believed to be responsible for the killing by leucocytes.

Many agents, both soluble and particulate, are able to activate the respiratory burst. Particular activating agents include bacteria, viruses and fungi for internal body organs or areas and bacteria, viruses, fungi, fibers, smoke, dust, ash, pollen, smog and the like for body cavities and organs such as the lungs, skin, digestive and excretory tracks that are open to the environment. Soluble agents can be toxins, medicinal compounds and soluble excretions of bacteria, fungi and infected mammalian cells and the like.

Activation of the respiratory burst in leucocytes usually follows exposure to the stimulus for less than a minute. Upon stimulation of the respiratory burst, the consumption of oxygen in leucocytes increases by over 100-fold resulting in, among other things, the production of superoxide, peroxide and hydrogen peroxide. The term "leucocytes" as used herein includes lymphocytes, phagocytes, macrophages and auxiliary cells.

Usually, after respiratory bursting, the stimulant and/or the mechanism of stimulation turns off allowing the leucocyte to return to its normal resting state. When the bursting does not turn off, the inflammatory action of the leucocytes continues unchecked causing a number of disease states. These disease states occur as the compounds produced by the leucocytes attack injure and kill tissue cells and other leucocytes. It is this failure to turn off the respiratory burst and the resulting injury to surrounding tissue cells, blood cells, other leucocytes and injured cells that produces the disease states treated by the present invention. Undesired inflammatory response occurs when the inflammatory response causes injury to host cells and this injury poses an independent threat to the host and healing cannot take place under these circumstances.

In a preferred embodiment, the therapeutic compositions containing an inflammatory suppressor are administered locally to the site of inflammation. In another preferred embodiment, the therapeutic compositions are administered systemically. In yet another preferred embodiment, the therapeutic compositions are administered systemically and locally concomitantly.

In a preferred embodiment, the therapeutic compositions are administered topically or by injection. Typically, the therapeutic compositions may be first applied by any suitable means. The therapeutic compositions may be in liquid or solid form or creams.

Preferably the inflammatory suppressor when brought into contact with a mammalian cell provides a cellular energy source and a building block in the cellular synthesis of other cellular components, while enhancing healing, cellular proliferation, deposition of the correct type and ratio of collagen and elastin.

The inflammatory response being reduced is or more one of the following, among others, oxygen radical production, peroxide production, cytokine and/or protease production, prostaglandin production, erythema, pain, tissue ischemia, excess angiogenesis, excess WBC infiltration, swelling, itching, crusting, histamine and interlukine production and like responses known in the art as inflammatory responses and scar formation.

The preferred inflammatory suppressor is at least one compound used singly or in combination selected from the group consisting of pyruvate, oxaloacetate, keto-glutarate, keto-butyrate, keto-adipate, keto-caproate, keto-isovalerate, their pharmaceutically acceptable salts and mixtures thereof. These may be used singly or in combination to produced the desired effect. Some of these keto acids work synergistically to enhance healing.

Preferred salts of the inflammation suppressor are salts that do not produce an adverse effect on the mammalian cell when applied as a salt of the inflammation suppressor. Typical salts would be the lithium, sodium, potassium, aluminum, magnesium, calcium, zinc, manganese, ammonium and the like and mixtures thereof.

Compositions for reducing and treating the disease state in mammals caused by the undesired inflammatory response comprise an inflammatory response suppressor in a pharmaceutically acceptable carrier composition. These may be formulated as any one of a number of delivery systems such as tablets, capsules, liquids, isotonic liquids, isotonic media, enteric tablets and capsules, parenterals, topicals, creams, gels, ointments, chewing gums, confections and the like.

The inflammatory suppressor is administered in a therapeutically effective amount to reduce the undesired inflammatory response. Preferably from 0.001 to 10 grams per dose. More preferably, 0.001 to 1 gram per dose and most preferably 0.001 to 0.25 grams per dose. It is understood that the method of administration and the condition being treated will greatly affect the dosage amount required to achieve the therapeutic effect.

Particular disease states to be treated include wounds, burns, sunburns, surgical procedures, chemical burns, decubitus ulcers, diabetic ulcers, arthritis, Parkinson's Disease, Alzheimer's Disease, Multiple Sclerosis (MS), spinal cord injuries, organ diseases where one has damage from ischemia and reperfusion damage, i.e., brain, liver, etc., hemorrhagic shock, organ transplants, gastrointestinal disorders, aging diseases, atherosclerosis, strokes, neurological diseases, as well as any type of wound resulting from laser treatments for the removal of scar and wrinkles.

The inflammatory suppressor of the present invention may be administered prior to, after and/or with other therapeutic agents. Typical therapeutic agents are antibacterials, antivirals, antifungals, antihistamines, proteins, enzymes, hormones, nonsteroidal anti-inflammatories, cytokines, antioxidants, fatty acids, anticancer agents, steroids, and the like.

The following examples are provided to better describe and more specifically set for the compositions and methods of treatment comprising the present invention. They are for illustrative purposes only, comprising the present invention. They are for illustrative purposes only, and it is recognized that many minor changes and/or alterations may be made with respect to the compositions and the amounts of the components employed that are not contemplated herein. It is to be understood however, that to the extent any such changes and/or variations do not materially change the formulation or functional attributes of the composition achieved, they are considered as following within the spirit and scope of the invention as recited in the following claims.

EXAMPLE 1

Fourteen wound sites were made on a patient's arm with strip tape which produces a shallow derm abrasion. The five keto acids were compared to a placebo-treated control, which only contained petrolatum by itself and a control which contained petrolatum with vitamin E and fatty acids. Time to healing was determined visually when redness and re-epithelization occurred.

|  | Control | | Keto-isovaleric | | keto-butyrate | | oxaloacetate | | keto-glutarate | | pyruvate | | pyruvate keto-isovaleric | |
|---|---|---|---|---|---|---|---|---|---|---|---|---|---|---|
|  | A | B | A | B | A | B | A | B | A | B | A | B | A | B |
| Days to healing re-epithelization | 5 | 4.5 | 4.0 | 2.5 | 4.5 | 4.0 | 3.5 | 3.0 | 5.5 | 5.0 | 3.0 | 2.0 | 3.5 | 2.0 |
| Days of crusting | 7 | 7 | 5 | 3 | 6 | 5 | 7 | 6 | 6 | 5.5 | 6 | 5 | 4 | 2 |
| Days of redness erythema | 9 | 8 | 6 | 5 | 9 | 7 | 9 | 6 | 10 | 9 | 8 | 6 | 5 | 3 |
| Days for disappearance of swelling | 4.0 | 3.0 | 3.5 | 2.5 | 4.0 | 3 | 3.5 | 2.5 | 4.0 | 3.5 | 3.5 | 2.5 | 2.5 | 1.0 |
| Days of itching | 6 | 5 | 4 | 3 | 5 | 4 | 5 | 4 | 7 | 5 | 5 | 4 | 4 | 3 |
| Days of pain | 5 | 5 | 3 | 2 | 4 | 4 | 4 | 3 | 5 | 4 | 4 | 3 | 2 | 1 |
| TOTAL SCORES | 36 | 32.5 | 25.5 | 18 | 32.5 | 27 | 32 | 24.5 | 37.5 | 33 | 29.5 | 21.5 | 21 | 12 |
| % Change from A Control | 0% | | +30% | | +10% | | +10% | | 0% | | +18% | | +42% | |
| % Change from B Control | 0% | | +45% | | +17% | | +25% | | −1% | | +34% | | +64% | |

Control A = petrolatum    B = petrolatum with vitamin E, fatty acids
A) petrolatum with active
B) petrolatum with active, vitamin E, fatty acids As can be seen from the results, keto-isovalerate produced the best results over all when compared to the controls (A & B) without the other keto acids and to the other keto acids with and without vitamin E and fatty acids. In most cases, the addition of vitamin E and fatty acids was shown to be synergistic with the keto acids with the exception of keto-glutarate. Pyruvate was the best in re-epithelization. Its ability was poor when it came to the reduction of crusting, erythema, itching and moderate in its ability to reduce pain. Keto-isovalerate was not as effective in its ability to enhance re-epithelization, but was superior in the reduction of crusting, erythema, itching, and pain. Unexpectedly, the combination of pyruvate and keto-isovalerate were synergistic and produced the best results in all categories. Oxaloacetate produced the best type of collagen deposition. Various keto acids could be mixed to varying effects.

There are a number of keto acids known in the art and whereas all are extracellular antioxidents. Each is unique in their interaction and effect on mammalian cells. Pyruvate enhances re-epithelization and angiogenesis of new capillaries. It has the ability to enter cells to protect cellular components including DNA. It works synergistically with other cellular components and reacts with $H_2O_2$ to produce acetate, a cellular energy source. It has been used in the past in the treatment of normal wounds.

EXAMPLE 2

Throughout medical history, there has been interest in shortening wound-healing by reducing the duration of associated symptoms as well as diminishing resultant scars. This study looks at wound-healing after cosmetic surgery, but is potentially applicable to a broad spectrum of wounds. Injured or stressed cells undergo free radical reactions more quickly than uninjured healthy cells. During wound healing, infiltrating leukocytes release activated oxygen species including $O_2$, $H_2O_2$, $OH^-$, and $^1O_2$. Various agents such as burns, ultraviolet light, ionizing radiation, toxic agents and drugs, and invading bacteria stimulate the release of these free radicals. Cells defend against free radicals by producing free radical scavengers and antioxidants. Antioxidants are the main antidote to oxygen free radicals. Known antioxidants include vitamin E, pyruvate, vitamin C, and other compounds and enzymes. These antioxidants may be depleted resulting in "un-neutralized" oxidative biochemical injuries. These injuries lead to a final common pathway that impairs and delays wound healing.

Laser skin resurfacing has become a very popular and prevalent cosmetic procedure to rejuvenate photoaged skin. Candidates for this procedure generally have a greater than average amount of photoaging and likely have depleted antioxidants. In addition, the greatest complaint surrounding these procedures is the long period of wound-healing and prolonged erythema pain, swelling, and crusting. Alster, et al. recently reported application of stabilized 10% topical L-ascorbic acid in aqueous formulation, which resulted in a significant decrease in post-carbon dioxide ($CO_2$) laser resurfacing erythema by the $8^{th}$ postoperative week when compared with laser-irradiated skin that had not received topical vitamin C.

The speed of wound-healing and the duration of erythema are the primary complaints after laser skin resurfacing. Antioxidants have been shown to enhance the healing of wounds by reducing free radical damage. Reepithelialization is also enhanced by the moist environment produced by occlusive dressings.

This residual thermal injury creates the desirable tissue tightening and collagen shrinkage, with minimal postoperative bleeding, but also results in the undesired postoperative pain, prolonged erythema, and the increasingly troublesome hypopigmentation that are characteristic of current $CO_2$, resurfacing procedures.

Laser resurfacing of facial rhytids has become a popular treatment option for many patients with wrinkles, photoaging, and acne scarring. Laser wavelength options and optimization of techniques continue to evolve in an attempt to shorten the healing phase associated with laser skin resurfacing.

The purpose of the study was to compare the effects of 5 alpha-keto acids for their effects on the rate of cutaneous healing. The wound model utilized was a split upper lip design wherein the wound was created by a well defined model of laser skin resurfacing. This model utilized pulsed $CO_2$ and Er: YAG lasers in a defined protocol (computerized scanner for $CO_2$ and uniform pulses with Er: YAG) which removes the entire stratum corneum and epidermis, as well as a uniform amount of dermis. Patient diaries were maintained to assess erythema, crusting, pain, itching, swelling, pigmentary changes, and the day of first make-up application. Blinded objective grading of improvement was independently assessed by 4 blinded observers at time intervals 3, 6, and 10 days, and 1, 2, and 4 months. Chromometer measurements of erythema were also analyzed and percentage moisture recorded A control that was utilized consisted of the same alpha-keto-wound balm without the active alpha-keto acid (that is pure petroleum, vitamin E, and egg yolk fatty acids). The product code is enclosed. Active agent were one of: alpha-keto-isovaleric acid, sodium salt; alpha-keto-butyric acid sodium salt; oxalacetic acid, sodium salt; alpha-keto-glutaric acid, sodium salt; sodium pyruvate. (Please note that sodium pyruvate is one of these 5 actives which has been studied in detail in the past and was known to accelerate wound healing.

Data analysis and diary information summaries:

Moisture analysis: Alpha-keto-butyric acid, sodium salt was by far the most effective while others had little effect on skin. This suggests that the stratum corneum barrier layer of the skin was less completely repaired than the other products (a negative).

Crusting analysis: There is a tendency for decreased duration of crusting (that is speed of wound healing) to be related to the length of the alpha-keto acids—that is it is possible that this is proportional to some molecular characteristic. This may also be mirrored in skin irritancy, and thus selected alpha-keto-isovaleric acid, sodium salt for expanded study.

Current laser skin resurfacing techniques averages 5–7 days to skin re-epithelialization (healing) whereas a few years ago, 10–14 days was typical. For ethical reasons, the selected the current "standard of care" model and thus the "delta value" for wound-healing between active and control should be greater/more significant for other types of wounds. Also, inevitably, some active contacts the control side in the upper lip model. Finally, the control—if it were plain petroleum—would have shown a greater difference. In short, these activities in all likelihood are more effective than these results show for typical "real world" wounds.

Redness: All laser wounds remain red for weeks to months. The study design did not address the final redness issue in the diaries, but rather we utilized a Minolta Chromometer to look at relative values of erythema. The "LAB" color space model was used wherein the "A" value correlates with erythema.

Irritation: Significant irritation would have been represented by a greater increase in the "A" value with one active compared to others. While significant differences were not noted during the study, pilot open patch testing data on known sensitive skinned individuals did show differences—some subjects developed red skin irritations and welt-like reactions (which I do consider significant). These actives were: alpha-keto-glutaric acid, sodium salt and slight reaction in one person to alpha-keto-butyric acid, sodium salt.

Pain: The increase in pain with alpha ketoglutarate was a notable event.

All 5 alpha-keto acid wound-healing formulations were effective in accelerating wound healing in the model. The pyruvate formulation has proven in extended clinical usage to be an effective product. This pilot screening study provides some insight into the relative efficacy of these 5 agents. Irritation was the only adverse event. Active agent alpha-keto-isovaleric acid, sodium salt was selected for further evaluation in more subjects based on my interpretation of this data, prior clinical experience with the pyruvate product, prior career knowledge, our own patch testing of the relative skin irritancy of some of these keto acids, and finally on the relative molecular size. Other of the activities are worthy of further clinical evaluation—in particular alpha-keto-butyric acid, sodium salt and possibly oxalacetic acid, sodium salt would be my choice.

EXAMPLE 3

Inhibition of Irritation and Cytotoxicity of Therapeutic Agents.

a) All seven of the enumerated keto acids were placed into a commercially available triple antibiotic ointment which was modified by also incorporating 4% vitamin E and 6% lecithin by weight. The keto acids were also placed individually into the same formula and were compared to a control consisting of the antibiotic ointment alone. Each formula was tested for healing rates and any associated irritation caused thereby on a patch of dermabraided skin. The triple antibiotic ointment without the keto acids produced an irritation of the skin from the antibiotics. The formulations with the keto acids did not. Time in which healing took place on the skin was enhanced by three days with the keto acid formulations.

b) The same formula was used to treat dry winter skin, where it worked to prevent winter itch, cracking and pain. Hydrocortisone was also formulated with the keto acids to also treat dry skin. This formula reduced redness and pain. A commercial cold sore formula was purchased and the seven enumerated keto acids were placed into it to treat cold sores, both as a combination and singly as well. The commercial formulation by itself was utilized as a control. The normal cold sore formulas with phenol, an antiviral agent, did not work very well. However, when keto acids are placed in the cold sore formulation either singly or in combination with other keto acids both with and without anti-oxidants and fatty acids, they heal the cold sore at a much faster rate when tested on a cold sore sufferer.

I claim:

1. A pharmaceutical composition for the reduction and treatment of a disease state of wound in mammals caused by an undesired inflammatory response comprising an effective amount of a combination of two inflammatory suppressor compounds together with a secondary therapeutic agent incorporated in a pharmaceutically acceptable carrier composition, wherein one of the inflammatory suppressor compounds is pyruvic acid, or its salt, and the other compound is keto-valeric acid, or its salt, and wherein the secondary therapeutical agent is selected from the group consisting of fatty acids and mixture thereof.

2. The composition of claim 1 wherein said inflammatory response being reduced is selected from the group consisting of oxygen radical production, hydrogen peroxide production, cytokine and protease production, prostaglandin production, excess angiogenesis, excess white blood cell infiltration, tissue ischemia, pain, swelling, itching, crusting, erythema, histamine and leukotriene production, scar formation and mixtures thereof.

3. The composition of claim 2 wherein said salt is selected from the group consisting of sodium, lithium, potassium, aluminum, magnesium, calcium, zinc, manganese, ammonium and mixtures thereof.

4. The composition of claim 1 wherein said inflammatory suppressor compound is a cellular energy source and a building block in the cellular synthesis of other cellular components.

5. The composition of claim 4 wherein said carrier composition is an isotonic media.

6. The composition of claim 5 wherein said carrier composition is selected from the group consisting of isotonic solutions, suspensions, injectables and topicals.

7. The composition of claim 6 wherein said disease state is selected from the group comprising wounds or other diseased states caused by ischemia or oxygen radical damage.

8. The composition of claim 7 wherein said disease state is a wound.

9. The composition of claim 7 wherein the composition is used following laser surgery or laser dermabrasion treatment to reduce erythema, swelling, crusting, scarring or pain.

10. The composition of claim 7 wherein the composition is delivered intravenously, topically or orally to reduce the effects of ischemia and/or oxygen radical damage.

11. The composition of claim 10 wherein the composition is formulated as a cosmetic used to alleviate, manage, or help the conditions of dry winter skin, winter itch, and skin cracking.

12. The composition of claim 11 further comprising hydrocortisone.

13. The composition of claim 12 wherein the disease state is any disease caused by oxygen radical damage.

14. The composition of claim 1 wherein said fatty acid is selected from the group comprising butyric acid, caproic acid, caprylic acid, capric acid, lauric acid, myristic acid, myristoleic acid, palmatic acid, palmitoleic acid, steric acid, oleic acid, linoleic acid, linolinic acid, arachidic acid, gadoleic acid and mixtures thereof.

* * * * *

UNITED STATES PATENT AND TRADEMARK OFFICE
CERTIFICATE OF CORRECTION

| | |
|---|---|
| PATENT NO. | : 7,122,578 B2 |
| APPLICATION NO. | : 09/950490 |
| DATED | : October 17, 2006 |
| INVENTOR(S) | : Martin |

It is certified that error appears in the above-identified patent and that said Letters Patent is hereby corrected as shown below:

Col. 22, lines 49-59, should read

1. A pharmaceutical composition for the reduction and treatment of a disease state of wound in mammals caused by an undesired inflammatory response comprising an effective amount of a combination of two inflammatory suppressor compounds together with a secondary therapeutic agent incorporated in a pharmaceutically acceptable carrier composition, wherein one of the inflammatory suppressor compounds is pyruvic acid, or its salt, and the other compound is alpha-keto-isovaleric acid, or its salt, and wherein the secondary therapeutical agent is selected from the group consisting of fatty acids and mixture thereof.

Signed and Sealed this

Second Day of October, 2007

JON W. DUDAS
*Director of the United States Patent and Trademark Office*